US006995248B2

(12) United States Patent
Lee et al.

(10) Patent No.: US 6,995,248 B2
(45) Date of Patent: Feb. 7, 2006

(54) IMMOBILIZATION OF NUCLEIC ACIDS

(75) Inventors: Kan-Hung Lee, Hsinchu (TW);
Kang-Jehng Chen, Hsinchu (TW);
Hsing Hsiao, Hsinchu (TW);
Shin-Hwan Wang, Hsinchu (TW)

(73) Assignee: Dr. Chip Biotechnology, Inc., Hsinchu (TW)

( * ) Notice: Subject to any disclaimer, the term of this patent is extended or adjusted under 35 U.S.C. 154(b) by 0 days.

(21) Appl. No.: 09/906,207

(22) Filed: Jul. 16, 2001

(65) Prior Publication Data

US 2003/0017561 A1   Jan. 23, 2003

(51) Int. Cl.
*C07H 21/00*   (2006.01)
*C07H 1/00*   (2006.01)
*C07K 17/08*   (2006.01)
*C12N 11/08*   (2006.01)

(52) U.S. Cl. .................... 536/22.1; 435/180; 530/402; 530/815; 536/124

(58) Field of Classification Search ................ 435/174, 435/177, 180, 181; 530/810, 815, 816; 230/402; 536/22.1, 124

See application file for complete search history.

(56) References Cited

U.S. PATENT DOCUMENTS

| | | | | |
|---|---|---|---|---|
| 3,849,253 | A | * 11/1974 | Harrey et al. | 435/182 |
| 4,614,714 | A | * 9/1986 | Kusakabe et al. | 435/25 |
| 4,764,466 | A | * 8/1988 | Suyama et al. | 435/174 |
| 5,789,219 | A | * 8/1998 | Bieniarz et al. | 435/188 |
| 5,981,734 | A | * 11/1999 | Mirzabekov et al. | 536/25.3 |
| 6,171,797 | B1 | 1/2001 | Perbost | 435/6 |
| 6,498,245 | B2 | * 12/2002 | Kimura et al. | 536/25.3 |

FOREIGN PATENT DOCUMENTS

| | | |
|---|---|---|
| EP | 0 390 500 A2 | 10/1990 |
| EP | 0 403 700 A1 | 12/1990 |
| EP | 0 390 500 A3 | 7/1992 |
| EP | 1 035 218 A1 | 9/2000 |
| WO | WO 96/35699 | 11/1996 |
| WO | WO 01/16372 | 3/2001 |
| WO | WO 01/40310 | 6/2001 |

OTHER PUBLICATIONS

Zaborsky, O., Immobilized Enzymes, CRC Press, Cleveland, Ohio, 1973, pp. 14, 15, 20, 25 & 27.*
Lemieux, et al., TIBTECH, vol. 16, Dec. 1998, pp. 506-513.*
Basu et al., "Solid Phase Synthesis of a D-Peptide-Phosphorothioate Oligodeoxynucleotide Conjugate from Two Arms of a Polyethylene Glycol-Polystyrene Support", Tetrahedron Letters 36:4943-4946, 1995.
Database WPI Section Ch. Week 199149 Derwent Publications Ltd., London, GB; AN 1991-356630, XP002195605 & JP 03 237147 A (Mitsubishi Kasei Vinyl KK), Oct. 23, 1991 abstract.
Yanzheng Xu and Eric T. Kool. *High sequence fidelity in a non-enzymatic DNA autoligation reaction*. Nucleic Acids Research, 1999, vol. 27, No. 3. pp. 875-881.

\* cited by examiner

*Primary Examiner*—David M. Naff
(74) *Attorney, Agent, or Firm*—Fish & Richardson P.C.

(57) ABSTRACT

This invention relates to a biomolecule-bound substrate made of polymeric molecules, each of which contains a reacting group; and a plurality of biomolecules, each of which contains another reacting group. One of the two reacting groups is a substitute group and the other is a leaving group; and the biomolecules are covalently bonded to the solid support via a chemical ligation reaction between the two reacting groups.

6 Claims, No Drawings

IMMOBILIZATION OF NUCLEIC ACIDS

BACKGROUND

Diagnostic assays and other chemical processes often require attaching a molecule to a solid support. For example, a protein is commonly attached to a solid support for an immune assay, and an oligonucleotide to a solid support for a hybridization-based assay. The attachment can be achieved in a number of different ways, including covalent bonding and non-covalent interaction. Typically, covalent attachment is more robust. See, for example, Lamture et al. (1994) *Oligonucleotide Research* 22: 2121–2125; Beattie et al. (1995) *Mol. Biotechnol.* 4: 213–225; Joos et al. (1997) *Anal. Biochem* 247: 96–101; Rogers et al. (1999) *Anal. Biochem.* 266: 23–30; and Chrisey et al. (1996) *Oligonucleotide Research* 24: 3031–3039.

A number of protocols have been developed to covalently attach an oligonucleotide to a support surface. One example achieves this by, e.g., synthesizing an oligonucleotide directly on a support surface using stepwise photolithographic reactions. For example, see U.S. Pat. Nos. 5,424,186; 5,510,270; and 5,744,305. Alternatively, a nucleic acid, such as a cloned cDNA, a PCR product, or a synthetic oligonucleotide, can be deposited onto a surface of a solid support, e.g., a microscopic glass slide, in the form of an array. Usually, the surface is modified in order to covalently attach a nucleic acid.

SUMMARY

In one aspect, this invention relates to a biomolecule-bound substrate that includes (1) a solid support made of polymeric molecules, each of which contains a reacting group; and (2) a plurality of biomolecules, each of which contains another reacting group. One of the two reacting groups is a leaving group and the other is a substitute group, and the biomolecules are covalently bonded to the solid support via a chemical ligation reaction between the two reacting groups. In other words, after the chemical ligation reaction, the leaving group departs from the biomolecules or the solid support, and the substitute group bridges the biomolecules and the solid support via a covalent bond. Each of the two just-described reacting groups refers to either its pre- or post-reaction state, depending on whether it participates in the reaction. Indeed, in a biomolecule-bound substrate of this invention, not all reacting groups on the substrate participate in the ligation reaction.

A leaving group is the group that departs from a molecule during a chemical ligation reaction. It can be, for example, halogen. A substitute group can be either a nucleophilic group or an electrophilic group. A nucleophilic group is a chemical species having unshared pair electrons (e.g., any Lewis base), and can be neutral or have a negative charge. Examples of the nucleophilic group include an oxygen-containing group (e.g., hydroxyl, alkoxy, or acyloxy), a sulfur-containing group (e.g., mercapto, alkylthio, sulfonate, or phosphorothioate), a nitrogen-containing group (e.g., amino, alkylamino, acylamino, nitro, azido, or isocyanato), and halogen. An electrophilic group is a chemical species having a vacant orbital for electrons to occupy, and can be neutral or have a positive charge. An example of the electrophilic group is an organometal.

A solid support used to practice this invention is made of at least one type of polymeric molecules evenly distributed throughout the solid support, each of which contains a leaving group or a substitute group. A solid support can be flexible and capable of being bent, folded, or otherwise manipulated without breakage. It can also be rigid and takes on a desirable configuration, such as film, sheet, tube, disc, or sphere. A porous solid support, such as gel, can also be used. Any of the just-described solid support can be used alone, or in combination with any other support (e.g., glass) well known in the art. Examples of a solid support for use in this invention include, but are not limited to, polyvinyl chloride resin (PVC), urea-formaldehyde resin, and acrylic. When a solid support is PVC resin, the chloride group in the PVC is a leaving group. A biomolecule containing a substitute group can react with the chloride group, resulting in covalently bonding of the biomolecule to the PVC resin. When a solid support is urea-formaldehyde resin, the amino group in urea-formaldehyde is a substitute group. A biomolecule containing a leaving group can react with the amino group, resulting in covalently bonding of the biomolecule to the urea-formaldehyde resin.

A biomolecule to be attached to the just-described solid support can be a biopolymer (e.g., an oligonucleotide, a peptide, a polysaccharide, or a glycoprotein) or a biomonomer (e.g., a nucleoside, an amino acid, or a monosaccharide), any of which can be a naturally occurring molecule or a synthetic analog. The term "oligonucleotide" used herein refers a synthetic DNA, a synthetic RNA, a cDNA, an mRNA, or a peptide nucleic acid. The biomolecule contains a leaving group or a substitute group, which, if not present naturally, must be introduced by chemical or biochemical methods well known in the art. A leaving group or a substitute group can locate at any suitable position of the biomolecule.

In another aspect, this invention relates to a method for preparing the afore-described biomolecule-bound substrate. The method includes (1) providing a solid support made of polymeric molecules, each of which contains a leaving group (or a substitute group); and a plurality of biomolecules, each of which contains a substitute group (or a leaving group); and (2) bonding the biomolecules to the solid support via a chemical ligation reaction between the leaving and substitute groups to form a biomolecule-bound substrate.

One advantage of this invention is that the surface of a solid support need not be modified in order to covalently attach a biomolecule. Other advantages, features, and objects of the invention will be apparent from the description and from the claims.

The details of one or more embodiments of the invention are set forth in the description below.

DETAILED DESCRIPTION

A biomolecule-bound substrate of this invention can be prepared by covalently bonding a biomolecule containing a substitute group to a solid support containing a leaving group. For example, one can deposit a phosphorothioate-containing oligonucleotide onto PVC resin. The phosphorothioate group, a substitute group, reacts with the chloride group, a leaving group, in the PVC to form an oligonucleotide-bound PVC resin. Shown below is a scheme that depicts this chemical ligation reaction.

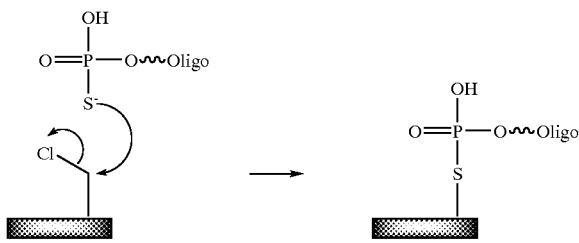

A biomolecule-bound substrate of this invention also can be prepared by covalently bonding a biomolecule containing a leaving group to a solid support containing a substitute group. For example, one can deposit an iodothymidine-containing oligonucleotide onto urea-formaldehyde resin. The amino group, a substitute group, in the urea-formaldehyde resin reacts with the iodo group, a leaving group, on the oligonucleotide to produce oligonucleotide-bound urea-formaldehyde resin. Shown below is a scheme that depicts this chemical ligation reaction.

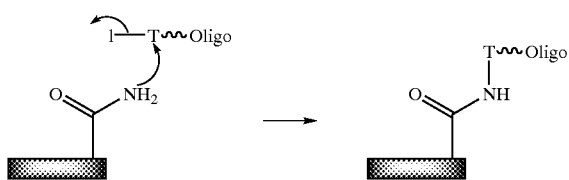

A biomolecule has a reacting group (i.e., a leaving group or a substitute group), which can locate at any suitable position. For example, an oligonucleotide has a reacting group at its the 3' or the 5' terminus, or at a non-terminal position. It can be immobilized onto a solid support and hybridize with its pair member. When the reacting group is at a non-terminal position, the oligonucleotide may be capable of forming a "hairpin" structure on the solid support to improve hybridization efficacy.

A biomolecule that contain a reacting group can be prepared using any convenient methodology. For example, wherein the biomolecule is an oligonucleotide, a number of protocols exist for introducing an oligonucleotide with a reacting group, if not present naturally. For instance, an oligonucleotide can be chemically synthesized on a DNA/RNA synthesizer using non-modified phosphoramidites, and a reacting group can be enzymatically added to one of the termini of the oligonucleotide. Alternatively, a modified phosphoramidite, with a reacting group, can be incorporated into a suitable position of an oligonucleotide using a DNA/RNA synthesizer. As another example, where the biomolecule is a peptide, it can be prepared chemically (e.g., on a peptide synthesizer) or biologically (e.g., expressed from a host cell). A functional group such as carboxy, hydroxy, phenoxy, amino, guanidino, or mercapto is present in peptides, and can serve as a reacting group. If an additional reacting group is needed, it can be introduced by, for example, incorporation of an amino acid analog.

Synthesis of a backbone-modified oligonucleotide, such as a phosphorothioate-containing oligonucleotide, is described in, for example, Krieg et al. (1995) *Nature* 374: 546–549; Weiner et al. (1997) *Proc. Natl. Acad. Sci. USA* 94: 10833–10837; and Boggs et al. (1997) *Antisense Nucleic Acid Drug Dev* 7(5): 461–471. Synthesis of a base-modified oligonucleotide, as well as other backbone-modified oligonucleotides (e.g., containing phosphorodithioate or aminoalkylphosphotriester), is described in, for example, U.S. Pat. No. 6,232,296.

A biomolecule can be bound to the solid support randomly, or in an order. The method of this invention can introduce a biomolecule, such as an oligonucleotide, a peptide, a polysaccharide, a nucleoside, an amino acid, or a monosaccharide, on a solid support in the form of an array, i.e., an orderly arrangement such as a matrix of rows and columns. An individual array can contain a number of unique attached biomolecules. The array may contain a plurality of addresses (each address being a unique attached biomolecule), and one or more unique attached molecules. Each addressable site can be directly adjacent to at least one other site, or can be separated from each other site, e.g., by a ridge, etch or surface lacking attached biomolecules. The array can have a plurality of addresses on the solid support. The density of the addresses is selected to provide for adequate resolution for detection, and can be at least 10, $10^3$, $10^5$, $10^7$ or $10^9$ addresses/$cm^2$, or no more than 10, $10^3$, $10^5$, $10^7$ or $10^9$ addresses/$cm^2$. The center to center distance between addresses can be 1 cm, 10 mm, 10 nm, 0.1 nm or less, or ranges between. The longest diameter of each address can be 1 cm, 10 mm, 10 nm, 0.1 nm or ranges between. Each address an contain 10 mg, 100 ng, 100 pg, 0.1 pg or less of the biomolecule, or ranges between. Alternatively, each address contains 100, $10^4$, $10^6$, $10^8$ or more biomolecules, or ranges between. The addresses can be distributed, on the substrate in one dimension, in two dimensions, or in three dimensions.

A biomolecule-bound substrate of this invention can be used in variety applications, where such applications are generally analytical in which the presence of a particular analyte in a given sample is detected at least qualitatively, if not quantitatively. More specifically, the sample suspected of containing the analyte of interest is contacted with the biomolecules on the solid support under conditions sufficient for the analyte to interact with its respective pair member that is present on the solid support. If the analyte of interest is present in the sample, it can form a complex with its pair member. The presence of the complex can be detected by, e.g., use of a signal production system such as an isotopic or fluorescent label present on the analyte.

An example of a biomolecule-bound substrate is an oligonucleotide array, in which a hybridization assay can be employed. The hybridization assay can be a gene discovery assay, a differential gene expression analysis assay, a sequencing assay, or an analysis of genomic polymorphism. For example, an oligonucleotide array can be used to produce gene expression profiles after polymerase mediated primer extension reactions. See, e.g., U.S. Pat. No. 5,262, 311; Liang, P & Pardee, A. B. (1992) *Science* 257; 967–971; Liang, P & Pardee, A. B. eds. (1997) *Methods in Molecular Biology*: Differential Display Methods and Protocols, Vol 85.). Such an array can be used, for example, to identify genes associated with diseases or screen compounds for drug discovery in a high throughput format. In particular, a high-density array has been proven to monitor gene expression, map genomic library clones, and resequence genes to screen for mutations and polymorphisms. For example, see, Ramsay (1998) *Nature Biotechnology* 16: 40–44; Bains and Smith (1988) *J. Theor. Biol.* 135:303–307; Drmanac et al. (1989) *Genomics* 4: 114–128; and Shena et al. (1995) *Science* 270: 467–470.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications, including patents, cited herein are hereby incorporated by reference in their entirety.

EXAMPLE 1

Preparation of an Oligonucleotide-bound Plastic Substrate

A 10 $\mu$M 3'-phosphorothioate and 5'-biotin modified oligonucleotide solution was prepared. 0.5 $\mu$L of the solution was spotted onto a plastic substrate made of PVC resin. The plastic chip was incubated at 32° C. overnight, washed with deionized distilled water (DDW), reacted with streptavidin-alkline phosphatase, and treated with a buffer containing nitroblue tetrazolium (NBT)/5-bromo-4-chloro-3-indolylphosphate (BCIP). The results indicate that oligonucleotide was covalently bound to the plastic substrate.

EXAMPLE 2

Preparation of an Oligonucleotide-bound Substrate

A 10 $\mu$M 3'-amino and 5'-biotin modified oligonucleotide solution was prepared. 0.5 $\mu$L of the solution was spotted onto a plastic chip made of PVC resin. The plastic substrate was incubated at 32° C. overnight, washed with DDW, reacted with streptavidin-alkline phosphatase, and treated with a buffer containing NBT/BCIP. The results indicate that oligonucleotide was covalently bound to the plastic substrate.

EXAMPLE 3

Hybridization of a Bound Oligonucleotide on a Plastic Substrate

A 10 $\mu$M 3'-phosphorothioate modified oligonucleotide solution was prepared. 0.5 $\mu$L of the solution was spotted onto a plastic chip made of PVC resin. The plastic substrate was incubated at 32° C. overnight, and washed with DDW. A biotin-labeled PCR product, containing a sequence complementary to the 3'-phosphorothioate modified oligonucleotide, was applied to the plastic substrate. After incubation, the chip was washed, reacted with streptavidin-alkline phosphatase, and treated with a detection buffer containing NBT/BCIP. The results showed that hybridization of the PCR product to the oligonucleotide on the substrate was efficient.

OTHER EMBODIMENTS

All of the features disclosed in this specification may be used in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Accordingly, other embodiments are also within the scope of the following claims.

What is claimed is:

1. A nucleic acid-bound resin substrate comprising:
   a nucleic acid covalently bonded to a polyvinyl chloride resin or to a urea-formaldehyde resin by a chemical ligation reaction between two reactive groups, wherein a reactive chloride group of the polyvinyl chloride resin leaves and is substituted by a reactive group of the nucleic acid, or a reactive group of the nucleic acid leaves and is substituted by a reactive amino group of the urea-formaldehyde resin.

2. The nucleic acid-bound resin substrate of claim 1, wherein the nucleic acid contains a reactive phosphorothioate group, and the chloride group of the polyvinyl chloride resin is substituted by sulfur of the phosphorothioate group.

3. The nucleic acid-bound resin substrate of claim 1, wherein the nucleic acid contains a reactive iodothymidine group, and iodine of the iodothymidine group is substituted by the amino group of the urea-formaldehyde resin.

4. A method for preparing a nucleic acid-bound resin substrate comprising:
   providing a polyvinyl chloride resin or a urea-formaldehyde resin; and
   covalently bonding a nucleic acid to the polyvinyl chloride resin or to the urea-formaldehyde resin by a chemical ligation reaction between two reactive groups, wherein a reactive chloride group of the polyvinyl chloride resin leaves and is substituted by a reactive group of the nucleic acid, or a reactive group of the nucleic acid leaves and is substituted by a reactive amino group of the urea-formaldehyde resin.

5. The method of claim 4, wherein the nucleic acid contains a reactive phosphorothioate group, and the chloride group of the polyvinyl chloride resin is substituted by sulfur of the phosphorothioate group.

6. The method of claim 4, wherein the nucleic acid contains a reactive iodothymidine group, and iodine of the iodothymidine group is substituted by the amino group of the urea-formaldehyde resin.

* * * * *